(12) United States Patent
Ratcliff et al.

(10) Patent No.: US 7,875,460 B2
(45) Date of Patent: Jan. 25, 2011

(54) METHOD FOR DETERMINING THE EFFECTIVENESS OF STABILIZED CHLORINE DIOXIDE IN A MOUTH RINSE

(75) Inventors: James L. Ratcliff, Pueblo West, CO (US); Elizabeth A. Renken, Peoria, AZ (US); Jessica K. Ward, Tempe, AZ (US)

(73) Assignee: Micropure, Inc., Scottsdale, AZ (US)

( * ) Notice: Subject to any disclaimer, the term of this patent is extended or adjusted under 35 U.S.C. 154(b) by 662 days.

(21) Appl. No.: 11/774,789

(22) Filed: Jul. 9, 2007

(65) Prior Publication Data

US 2009/0017548 A1    Jan. 15, 2009

(51) Int. Cl.
 *G01N 33/00* (2006.01)
 *G01N 30/02* (2006.01)
 *C01B 11/02* (2006.01)
 *G01N 30/90* (2006.01)
 *G01N 1/18* (2006.01)

(52) U.S. Cl. ............... 436/124; 422/70; 436/161; 436/178; 73/23.39; 423/477

(58) Field of Classification Search .......... 436/124
See application file for complete search history.

(56) References Cited

U.S. PATENT DOCUMENTS

| | | | |
|---|---|---|---|
| 2,451,897 A | 10/1948 | Woodward | 99/111 |
| 2,482,891 A | 9/1949 | Astori | 252/187 |
| 3,271,242 A | 9/1966 | McNicholas | 424/65 |
| 4,689,215 A | 8/1987 | Ratcliff | 424/53 |
| 4,696,811 A | 9/1987 | Ratcliff | 424/53 |
| 4,786,492 A | 11/1988 | Ratcliff | 424/53 |
| 4,788,053 A | 11/1988 | Ratcliff | 424/53 |
| 4,792,442 A | 12/1988 | Ratcliff | 424/53 |
| 4,793,989 A | 12/1988 | Ratcliff | 424/53 |
| 4,808,389 A | 2/1989 | Ratcliff | 424/53 |
| 4,818,519 A | 4/1989 | Ratcliff | 424/53 |
| 4,837,009 A | 6/1989 | Ractliff | 424/53 |

(Continued)

OTHER PUBLICATIONS

American Dental Association, Fluoridation Facts. 2005.

(Continued)

*Primary Examiner*—Jill Warden
*Assistant Examiner*—Jennifer Wecker
(74) *Attorney, Agent, or Firm*—The von Hellens Law Firm, Ltd.

(57) ABSTRACT

A method for determining the available treatment dosage of stabilized chlorine dioxide in the prevention and the treatment of plaque accumulation, volatile sulfur compound production, gingivitis and periodontitis, and for differentiating the treatment dosage from other chlorine-containing compounds that may not have such beneficial effects is disclosed. When in solution as stabilized chlorine dioxide, the presence of other ions such as chlorate and chloride may not only obscure results as to the concentration of stabilized $ClO_2$, but also reduce the predicted effectiveness. The present invention uses validated analytical methods to predict the effectiveness of stabilized $ClO_2$ by more precisely measuring its concentration in solution. Such measurement renders precision at a level required of food-grade and pharmacy-grade chemotherapeutic agents in the oral cavity. Preferred concentrations are within the range of about 0.005 to about 2% (w/v) stabilized chlorine dioxide. The solution may be in the form of wash, rinse, soak, paste, gel, aerosol spray, or other suitable delivery system.

16 Claims, 12 Drawing Sheets

U.S. PATENT DOCUMENTS

| | | | | |
|---|---|---|---|---|
| 4,851,213 | A | 7/1989 | Ratcliff | 424/53 |
| 4,855,135 | A | 8/1989 | Ratcliff | 424/127 |
| 4,886,657 | A | 12/1989 | Ratcliff | 415/53 |
| 4,889,714 | A | 12/1989 | Ratcliff | 424/53 |
| 4,925,656 | A | 5/1990 | Ratcliff | 424/53 |
| 4,975,285 | A | 12/1990 | Ratcliff | 424/661 |
| 5,192,691 | A * | 3/1993 | Quinn et al. | 436/161 |
| 5,200,171 | A | 4/1993 | Ratcliff | 424/52 |
| 5,348,734 | A | 9/1994 | Ratcliff | 424/53 |
| 5,489,435 | A | 2/1996 | Ratcliff | 424/422 |
| 5,618,550 | A | 4/1997 | Ratcliff | 424/422 |
| 5,738,840 | A | 4/1998 | Richter | 424/53 |
| 5,811,115 | A | 9/1998 | Ratcliff | 424/422 |
| 5,834,003 | A | 11/1998 | Ratcliff | 424/422 |
| 5,902,575 | A | 5/1999 | Ratcliff | 424/78.02 |
| 6,017,554 | A | 1/2000 | Ratcliff | 424/422 |
| 6,136,348 | A | 10/2000 | Ratcliff | 424/661 |
| 6,231,830 | B1 | 5/2001 | Madray | 423/477 |
| 2003/0066336 | A1 * | 4/2003 | Kotsuka et al. | 73/23.39 |

OTHER PUBLICATIONS

Armitage GC. Clinical evaluation of periodontal disease.: *Periodontal 2000* 1995; 7:39-53.

Baehni PC, Takeuchi Y. "Anti-plaque agents in the prevention of biofilm-associated oral diseases." *Oral Diseases* 2003; 9 (suppl I):23-29.

Barnhart WE, et al. "Dentifrice Usage and Ingestion Among Four Age Groups." *J Dent Res* 1974; 53:1317-1322.

Marsh PD. Dental Plaque: biological significance of a biofilm and community life-style. *J Clin Periodontal.* 2005; 32(Suppl. 6): 7-15.

Masschelein, WJ. *Chlorine Dioxide: Chlorine and Environmental Impact of Oxychlorine Compounds.* (1979) Anne Arbor: Ann Arbor Science Publishers, Inc.

Michael GE, et al. "Chlorine Dioxide Water Disinfection: A Prospective Epidemiology Study." *Arch Environ Health* 1981; 36:20-27.

Rose LF, Mealey BL, Genco, RJ, and Cohen DW. *Periodontics: Medicine, Surgery, and Implants.* (2004) St. Louis: Mosby, Inc.

Silwood CJL, Grootveld MC, Lynch E. A multifactorial investigation of the ability of oral health care products (OHCPs) to alleviate oral malodour. *J Clin Periodontol.* 2001; 28:634-641.

United States Environmental Protection Agency, Alternative Disinfectants and Oxidants Guidance Manual. 1999.

Daniel FB, et al. "Comparative Subchronic Toxicity Studies of Three Disinfectants." *J Am Water Works Ass* 1990: 10:61-69.

International Search Report, Jun. 20, 2008, 4 pages.

* cited by examiner

Table 1
Preparation of Solutions for IC Test:

Borate/Gluconate Concentration:
    Add        500 mL deionized water to beaker (1000 mL capacity)
    Dissolve   16 g Sodium Gluconate
                  18 g Boric Acid and
                  25 g Sodium Tetraborate Decahydrate.
    Add        250 mL Glycerine.
    Add        deionized water to fill to 1000 mL.
    Mix well, store in refrigerator.

Mobile Phase Eluent:
    Add        500 mL deionized water to beaker (1000 mL capacity)
    Transfer   20 mL Borate/Gluconate concentration
    Add        20 mL 1-Butanol and
                  120 mL Acetonitrile.
    Add        deionized water to fill to 1000 mL.
    Degas solution by filtering through 0.45 μm filter.
    Bring to pH 8.5 ± 0.05 with 0.1 $N$ NaOH.

Reference Stock Solution:
    Transfer   5.0 mL reference material (Anthium Dioxide® in this case) to flask (50 mL capacity)
    Add        mobile phase to fill to 50 mL.

Intermediate Stock Solution:
    Transfer   5.0 mL Reference Stock Solution to flask (50 mL capacity)
    Add        mobile phase to fill to 50 mL.

Standard Solution:
    Transfer   4.0 mL Intermediate Stock Solution to flask (100 mL capacity)
    Add        mobile phase to fill to 100 mL.
    Mix well, use within 12 hours.

Intermediate spike solution:
    Dissolve   33 mg sodium chloride (or other compound) to flask (25 mL capacity)
    Add        mobile phase to fill to 25 mL.
    Mix well.

Suitability Solution
    Transfer   1.0 mL intermediate spike solution to flask (50 mL capacity)
    Transfer   2.0 mL intermediate stock solution
    Add        mobile phase to fill to 50 mL.

Assay Standard Solution:
    Transfer   5.0 mL sample formulation to flask (50 mL capacity)
    Add        mobile phase to fill to 50 mL.

Assay Solution:
    Transfer   5.0 mL Assay Standard solution to flask (25 mL capacity)
    Add        mobile phase to fill to 25 mL.

Table 2

Recovery Results for Chlorite

| % target, sample | area (µV*sec) | avg. area (µV*sec) | % recovery | % recovery from control | average % recovery |
|---|---|---|---|---|---|
| 80 - I | 518000 / 517020 | 517510.0 | 97.2 | 100.01 | 100.0 |
| 80 - II | 516300 / 518080 | 517190.0 | 97.2 | 99.95 | |
| 90 - I | 580520 / 577620 | 579070.0 | 108.8 | 100.14 | 100.1 |
| 90 - II | 578705 / 577760 | 578232.5 | 108.7 | 99.99 | |
| 100 - I | 641410 / 640200 | 640805.0 | 120.4 | 100.27 | 100.2 |
| 100 - II | 638710 / 639865 | 639287.5 | 120.1 | 100.03 | |
| 110 - I | 700300 / 695385 | 697842.5 | 131.1 | 99.71 | 99.8 |
| 110 - II | 698585 / 699540 | 699062.5 | 131.4 | 99.88 | |
| 120 - I | 762960 / 758840 | 760900.0 | 143.0 | 100.03 | 100.2 |
| 120 - II | 760095 / 766510 | 763302.5 | 143.4 | 100.35 | |

Table 3

| sample | area (µV*sec) | % recovery | average % recovery |
|---|---|---|---|
| C1-I | 576000 | 109.06 | 109.5 |
| | 580860 | 109.98 | |
| C1-II | 571600 | 108.22 | 108.3 |
| | 572040 | 108.31 | |
| C1-III | 572820 | 108.45 | 108.3 |
| | 571630 | 108.23 | |
| C1-IV | 580670 | 109.94 | 110.1 |
| | 582320 | 110.25 | |
| C1-V | 590090 | 111.72 | 111.9 |
| | 592460 | 112.17 | |
| C1-VI | 573465 | 108.58 | 108.6 |
| | 573330 | 108.55 | |
| | | average | 109.5 |
| | | % RSD | 1.3 |

Table 4

| sample | area (µV*sec) | % recovery | average % recovery |
|---|---|---|---|
| C2-I | 564470 | 108.31 | 108.3 |
|  | 564780 | 108.37 |  |
| C2-II | 558370 | 107.14 | 106.8 |
|  | 554650 | 106.42 |  |
| C2-III | 559590 | 107.37 | 106.8 |
|  | 553830 | 106.26 |  |
| C2-IV | 547630 | 105.08 | 105.0 |
|  | 546300 | 104.82 |  |
| C2-V | 557075 | 106.89 | 106.3 |
|  | 550575 | 105.64 |  |
| C2-VI | 561350 | 107.71 | 108.0 |
|  | 564140 | 108.24 |  |
|  |  | average | 106.9 |
|  |  | % RSD | 1.1 |

Table 5

| sample | average % recovery |
|---|---|
| C1-I | 109.5 |
| C1-II | 108.3 |
| C1-III | 108.3 |
| C1-IV | 110.1 |
| C1-V | 111.9 |
| C1-VI | 108.6 |
| C2-I | 108.3 |
| C2-II | 106.8 |
| C2-III | 106.8 |
| C2-IV | 105.0 |
| C2-V | 106.3 |
| C2-VI | 108.0 |
| average | 108.2 |
| % RSD | 1.7 |

Table 6

| type of test | % RSD for detector response | resolution | % RSD for retention time |
|---|---|---|---|
| Linearity of Response | 2.79 | 9.6 | 0.1 |
| Assay Range | 0.31 | 9.6 | 0.0 |
| Accuracy Recovery | 0.17 | 9.3 | 0.0 |
| Precision: Chemist 1 | 0.97 | 9.0 | 0.0 |
| Precision: Chemist 2 | 0.51 | 9.0 | 0.0 |
| Specificity | 0.31 | 9.0 | 0.2 |

METHOD FOR DETERMINING THE EFFECTIVENESS OF STABILIZED CHLORINE DIOXIDE IN A MOUTH RINSE

BACKGROUND OF THE INVENTION

1. Field of the Invention

The present invention is directed to a method for confirming the effective dosage level of chlorine dioxide in a solution in the form of a wash, rinse, soak, paste, gel, aerosol spray, or other suitable delivery system while allowing differentiation of chlorine dioxide from ions that may interfere with the activation.

2. Description of Prior Art

Oral Disease

Oral disease refers to a number of generally preventable conditions of the mouth resulting from a variety of causes. Plaque is the most recognizable precursor to oral disease. It is the biofilm that forms on teeth within hours after they are cleaned. The main mineral component of teeth is hydroxyapatite (HAP) and when teeth are cleaned, HAP becomes exposed to the oral environment. Salivary proteins such as mucins, proline-rich proteins, statherins, histatins, and cystatins have a strong affinity for HAP. These proteins quickly bind or adsorb to the exposed HAP of the tooth to form a thin coating called the acquired pellicle. Certain bacteria in the oral cavity selectively adhere to the pellicle, begin to divide, and form colonies. Initially, approximately 80% of the bacteria that colonize pellicle-coated tooth surfaces are facultative, gram-positive, non-motile cocci such as *Streptococcus sanguinis* (formerly *Streptococcus sanguis*). The other 20% include a variety of gram-negative bacteria such as *Veillonella* species. As the colonies grow, the environment changes due to the metabolic activities of these early colonizers and the addition of diverse groups of other bacteria to the biofilm (plaque) mass.

An important environmental change in the plaque biofilm is the lowering of the local oxidation-reduction potential thus creating a low-oxygen environment that promotes the colonization and growth of anaerobic bacteria. Microorganisms in the biofilm synthesize a slime matrix or glycocalyx from the abundant polysaccharides, glycoproteins, and dietary sugars (e.g., sucrose) present in the oral environment. Eventually, the plaque becomes a characteristic biofilm with a highly structured, matrix-embedded, diverse microbial population in which gene expression is severely altered.

The volume and structure of the biofilm created provides protection to the bacteria housed within it, potentially reducing the efficacy of antimicrobials. As a result, disruption of the biofilm of plaque is typically accomplished by mechanical means (e.g., brushing, flossing, professional tooth cleaning). Use of certain anti-plaque and antiseptic agents has been suggested for prevention of biofilms, but these treatments are typically tested in vitro using pure strains of microbes cultured on agar. Such in vitro conditions do not adequately simulate the biofilm environment, which may limit the significance of the test results.

Within biofilms, continuous metabolic activity of bacteria produces acids that can demineralize tooth enamel and dentin leading to the development of dental caries and progressive tooth decay. This demineralization is irreversible unless there is early intervention by a dental professional who might recommend the inclusion of certain fluoride-containing oral care products in the daily dental routine. If left untouched, demineralization can progress to the inner layers of the tooth, leading to severe pain and increased potential for loss of the tooth.

If dental plaque is left undisturbed, deeper portions of the plaque biofilm mineralize leading to the formation of calculus. Calculus has two major components, organic material and inorganic material. The organic portion of calculus consists mainly of dead bacteria. The inorganic part of calculus is composed of several minerals derived from calcium and phosphate present in the oral environment. There are two types of calculus, subgingival (below the gum line) and supragingival (above the gum line). Supragingival calculus is highly organized, porous, and visible. Once formed, calculus cannot be removed by conventional brushing and flossing; the intervention of a dental professional is generally required. Calculus retention is problematic for oral health because it harbors biofilm-forming bacteria that can lead to the development of periodontal (gum) infections.

*Halitosis* (bad breath) is caused primarily by the presence of volatile sulfur compounds (VSCs) in expired breath. Approximately 90% of foul odors in expired mouth air are due to the presence of the two major VSCs: hydrogen sulfide ($H_2S$) and methyl mercaptan ($CH_3SH$—also called methanethiol). The sulfur in these VSCs comes from the breakdown by bacteria of sulfur-containing proteins from saliva, plaque, and sloughed epithelial cells. Increased production or build-up of any of the protein sources will lead to higher levels of VSCs in mouth air.

There are a number of known situations that will lead to increased VSC production. For example, persons who do not perform adequate oral hygiene will have abundant amounts of supragingival and subgingival plaque biofilms on their teeth. This is especially true in difficult-to-clean locations such as interproximal areas between the teeth. In addition, natural teeth that support some dental prostheses are difficult to clean. Finally, the dorsal surface of the tongue is rough, irregular, and harbors large quantities of microorganisms. In general, the microorganisms in chronic intraoral biofilms will produce large quantities of VSCs. Besides being the major contributor to halitosis, VSCs are potent irritants and can aggravate existing inflammation of the gums. High levels of VSCs can kill epithelial cells that may lead to increased permeability and ulceration of the gum tissue. The existence of open wounds coupled with increased gum tissue permeability can promote the entry of bacteria into the bloodstream (i.e., bacteremia). Chronic bacteremia may increase the risk for the development of a number of systemic problems such as heart attacks, stroke, and adverse birth outcomes.

Gingivitis is defined as the presence of gingival inflammation without loss of connective tissue attachment. The precursor to gingivitis is undisturbed dental plaque biofilms. Studies have shown that gingivitis will develop within 10-21 days if all oral hygiene practices are stopped and plaque is allowed to accumulate undisturbed. Clinical signs of gingivitis are redness, swelling (edema), and bleeding gums.

Periodontitis refers to a group of infections in which the supporting tissues of the teeth such as connective tissue and bone are destroyed by plaque-induced inflammation. The most common form is known as Chronic Periodontitis that affects approximately 20% of the adult U.S. population. Signs of chronic periodontitis include all of those associated with gingivitis (i.e., redness, swelling, bleeding) plus the formation of deep periodontal pockets (increased probing depths), gingival recession, increased tooth mobility, and loss of bone as detected by radiographs. If left untreated, chronic periodontitis can lead to tooth loss. Chronic periodontitis is a multifactorial disease in which host susceptibility to infections and multiple groups of bacteria are etiologically important. Factors that increase susceptibility to intraoral infections such as poor oral hygiene, smoking, diabetes mellitus, emotional stress, and innate (genetic) host responses to bacterial challenges also increase the risk of developing chronic periodontitis. Several dozen types of oral bacteria have been implicated as putative periodontal pathogens including gram-negative bacteria such as: *Porphyromonas gingibalis, Aggregatibacter actinomycetemcomitans, Tannerella forsythia, Eikenella corrodens, Prevotella intermedia*, and *Campylobacter rectus*. Gram-positive bacteria of importance include *Streptococcus intermedius, Micromonas micros*, and *Eubacterium* species. Spirochetes such as *Treponema denticola* are also important. Low levels of most of these pathogens can be isolated from healthy mouths. These bacteria only become a problem when they are left undisturbed in mature dental plaque biofilms. Finally, chronic periodontitis is a polymicrobial infection with multiple bacteria working together in a biofilm to cause the disease.

Treatment of both gingivitis and chronic periodontitis is designed to facilitate the frequent removal and disruption of dental plaque biofilms. For gingivitis, effective oral hygiene practices on a daily basis are usually sufficient. This involves thorough removal of plaque from facial and lingual surfaces of the teeth with a toothbrush and good interproximal care with dental floss or other appropriate devices (e.g., toothpicks). Periodic tooth cleaning by an oral health care provider is required to remove mineralized plaque (i.e., calculus). Treatment of chronic periodontitis is more difficult since the disease-causing plaque is usually at subgingival sites and in deep periodontal pockets. Standard interventions usually include oral hygiene instructions followed by thorough subgingival debridement (i.e., scaling and root planing). If the infection persists, surgical intervention may be recommended to reduce the depth of the pockets and to gain access to thoroughly remove the calculus deposits on root surfaces. In some cases, reconstructive surgical procedures are performed in an attempt to regain some of the lost periodontal attachment and supporting bone. Once the infection is under control, the patient is placed on a rigorous maintenance/recall program to reduce the chances of recurrent infection. It is during this maintenance phase of therapy that non-invasive over-the-counter products are especially useful in slowing down the reformation of dental plaque biofilms on tooth surfaces. Current over-the-counter anti-plaque and anti-gingivitis products do not meet all of the needs of consumers. On the other hand, prescription mouth rinses such as those containing chlorhexidine gluconate are effective treatments for gingivitis, but are not intended for long-term use, may stain teeth, and have an unpleasant taste. An example of a non-prescription mouth rinse sold under the trademark is Listerine®, which has been granted the ADA seal of approval as an anti-plaque and anti-gingivitis product. However, the high alcohol content and harsh taste of the formulation can be unpleasant for some consumers.

The use of chlorine dioxide for sanitation was first suggested in 1948 by Eric Woodward to reduce the incidence of unpleasant taste in shrimp. Since then, chlorine dioxide use has spread into a number of other industries. The oxidative power of $ClO_2$ is used in the manufacturing of wood pulp as an agent for the bleaching of cellulose fibers. In water treatment, $ClO_2$ has become widely used for water sanitation. It has been shown to be effective at reducing the bacterial content, algae content, and odor associated with wastewater treatment. Additionally, the utilization of $ClO_2$ for treating drinking water has been effective without adversely affecting its taste. The benefits of $ClO_2$ over other processes utilizing ozone or bleach for example, are reduced cost, reduced toxicity and reduced production of chlorinated by-products.

In 1999 the EPA published "Alternative Disinfectants and Oxidants Guidance Manual," describing disinfectant uses for $ClO_2$ and containing information on the mechanism of generation, application and standards and regulations governing use of $ClO_2$ and other disinfectants. Major applications listed by table 4-5, section 4.8.2 in the manual are as follows: primary or secondary disinfectant, taste control, odor control, TTHM/HAA reduction (total trihalomethanes are chlorinated organics, chloroform [$CHCl_3$] and dichlorobromomethane [$CHCl_2Br$] for example; haloacetic acids are created when an atom from the halogen group, chlorine, for example, replaces a hydrogen on the acetic acid molecule), Fe and Mn control, color removal, sulfide destruction, phenol destruction and Zebra mussel control [EPA 1999, p. 4-34]. These are accomplished by oxidation of various substances found in water. For example, unpleasant tastes and odors (sulfides, phenols, others) can exist in water due to vegetative decay and algae content. $ClO_2$ reduces these tastes either by eliminating the source (algae) or oxidizing the causative taste and odor molecules. In the control of iron and manganese, $ClO_2$ will bring the dissolved ions out of solution to form precipitates, which may be eliminated through filtration and/or sedimentation. Zebra mussel control is important because it helps to maintain the natural ecology of a body of water. Zebra mussels are organisms that will infest a lake or river, strip it of nutrients and create a pseudo-fecal mucous layer on the bottom. The use of $ClO_2$ for water sanitation and pulp treatment generally involves on-site generation followed by immediate use.

The term 'stabilized chlorine dioxide' on the other hand, refers to the generation and subsequent sequestration of $ClO_2$, which allows for its storage and availability for later use. The first reference to stabilized chlorine dioxide in patent was in U.S. Pat. No. 2,482,891 in which $ClO_2$ is stabilized in a powder for storage. For its application, it is mixed with water to "liberate" the chlorine dioxide. A method and composition for the use of aqueous stabilized chlorine dioxide for antiseptic purposes was noted in U.S. Pat. No. 3,271,242. The 1979 text Chlorine Dioxide, Chemistry and Environmental Impact of Oxychlorine Compounds, describes (aqueous) stabilized chlorine dioxide as follows:

"The stabilization of chlorine dioxide in aqueous solution was proposed by using perborates and percarbonates. Thus, a stabilized solution of $ClO_2$ would be obtained at pH 6 to 8 by passing gaseous $ClO_2$ into an aqueous solution containing 12% $Na_2CO_3.3H_2O_2$. Other variants are possible. In reality, it seems that in these methods, the chlorine dioxide is practically completely transformed to chlorite. Dioxide is released upon acidification . . . " [Masschelein, 1979]

The reference to percarbonates and perborates may be replaced by the term 'peroxy compounds,' which would refer to any buffer suitable for maintaining the pH and hence, the stability of the $ClO_2$ in solution. The buffer is a necessary component, as the $ClO_2$ is unstable at low pH. Once the solution reaches low pH or encounters an area of low pH, the stabilized $ClO_2$ is released from solution and available for sanitation and oxidation.

In oral care products, the use of stabilized $ClO_2$ has been suggested as an active ingredient by a number of patents: U.S. Pat. Nos. 4,689,215; 4,696,811; 4,786,492; 4,788,053; 4,792,442; 4,793,989; 4,808,389; 4,818,519; 4,837,009; 4,851,213; 4,855,135; 4,886,657; 4,889,714; 4,925,656; 4,975,285; 5,200,171; 5,348,734; 5,489,435; 5,618,550. Additionally, the use of stabilized $ClO_2$ has been suggested for the degradation of amino acids in U.S. Pat. No. 6,136,348. The premise for these products is that the stabilized chlorine dioxide will remain as such until it encounters the localized reductions in pH. Reduced pH levels can be a result of low pH saliva or oral mucosa, the accumulation of oral disease-causing bacteria or the presence of plaque biofilms on teeth and epithelial cells. Once released, the now active chlorine dioxide is effective at killing bacteria and oxidizing VSCs. Data have shown dramatic reduction in bacteria after exposures as short as 10 seconds, as set forth in U.S. Pat. No. 4,689,215. Additional data show remarkable decrease in VSCs in expired mouth air; the mechanism is believed to be oxidation of VSCs through the cleavage of the sulfide bonds.

The effectiveness of the chlorine dioxide is likely dependent on the amount of $ClO_2$ released from stabilized chlorine dioxide when the solution is acidified. The amount of $ClO_2$ released depends on the initial concentration of the solution, its pH, and the stabilizing buffer or agent used. It could follow that that the efficacy of the chlorine dioxide as an oral care product is dependent on the amount of $ClO_2$ released from the stabilized chlorine dioxide solution. As a result, it is imperative that accurate, precise measurements are taken so the concentration of stabilized $ClO_2$ and of the release of $ClO_2$ from solution can be determined. In addition to the need to quantify the efficacy of the solution, concentrations must be understood to ensure the safety of the product.

A concern about the stability of stabilized $ClO_2$ was recited in U.S. Pat. No. 5,738,840 with reference to the inclusion of "other oxychlorine species" which could refer to chloride [$Cl^-$] or chlorate [$ClO_3^-$]. The mechanism of action was questioned and suggested that at pH between 6.2 and 7.0 "any molecular chlorine dioxide which forms by degradation of the chlorite is converted back to chlorite by reaction with the residual stabilizer." This reverse reaction is unlikely due to the lower pH in the bacteria-laden target areas of the mouth described earlier. U.S. Pa. No. 6,231,830 calls into question the stoichiometry and safety of the formulation presented in U.S. Pat. No. 5,738,840. It is claimed that the formulation described is a 'chlorinator' in which " . . . a build-up of chlorate ion, an unwanted by-product" may occur.

The analytical methods for measurement recited in U.S. Pat. Nos. 5,738,840 and 6,231,830 are important to note. In the patent '840, the concentration was determined using spectrophotometry. No reference was made as to the use of a chemical indicator such as Chorophenol Red, as is used in typical analytical tests for chlorine dioxide content. The wavelength used was 360 nm, which is in the ultraviolet part of the electromagnetic spectrum. The only type of measurement in the patent '830 seemed to be a visual observation of brown tint from free iodine in samples. Neither method provided sufficient means to determine the dosage of active ingredient and the dosage of undesirable and potentially dangerous chlorates and chlorides.

SUMMARY OF THE INVENTION

The present invention relates to a method for determination of the effectiveness of stabilized chlorine dioxide as a pharmaceutically acceptable topical oral care product, including washes, rinses, soaks, pastes, gels, and aerosol sprays. Making the determination of active ingredient concentration without the interference of degradation products allows for a direct correlation to the expected efficiency of the active ingredient against conditions of the oral cavity associated with oral disease including, but not limited to, plaque accumulation, volatile sulfur compound production, gingivitis and periodontitis.

It is therefore a primary object of the present invention to provide a method for testing the concentration of chlorine dioxide ($ClO_2$) to be used as an effective topical oral care product.

Another object of the present invention is to provide a method for validating the test results of chlorine dioxide ($ClO_2$) as an oral care product.

Still another object of the present invention is to provide a method for determining the amount of chlorine dioxide released from stabilized chlorine dioxide upon acidification of the stabilized chlorine dioxide.

Yet another object of the present invention is to provide a method for precise measurement of the concentration of stabilized chlorine dioxide to determine the release of chlorine dioxide ($ClO_2$) from solution upon acidification.

A further object of the present invention is to provide a method for quantifying the efficacy of a solution of stabilized chlorine dioxide as an oral care product.

These and other objects of the present invention will become apparent to those skilled in the art as the description proceeds.

BRIEF DESCRIPTION OF THE DRAWINGS

The present invention will be described with greater specificity and clarity with reference to the drawings, in which.

Figure 1:
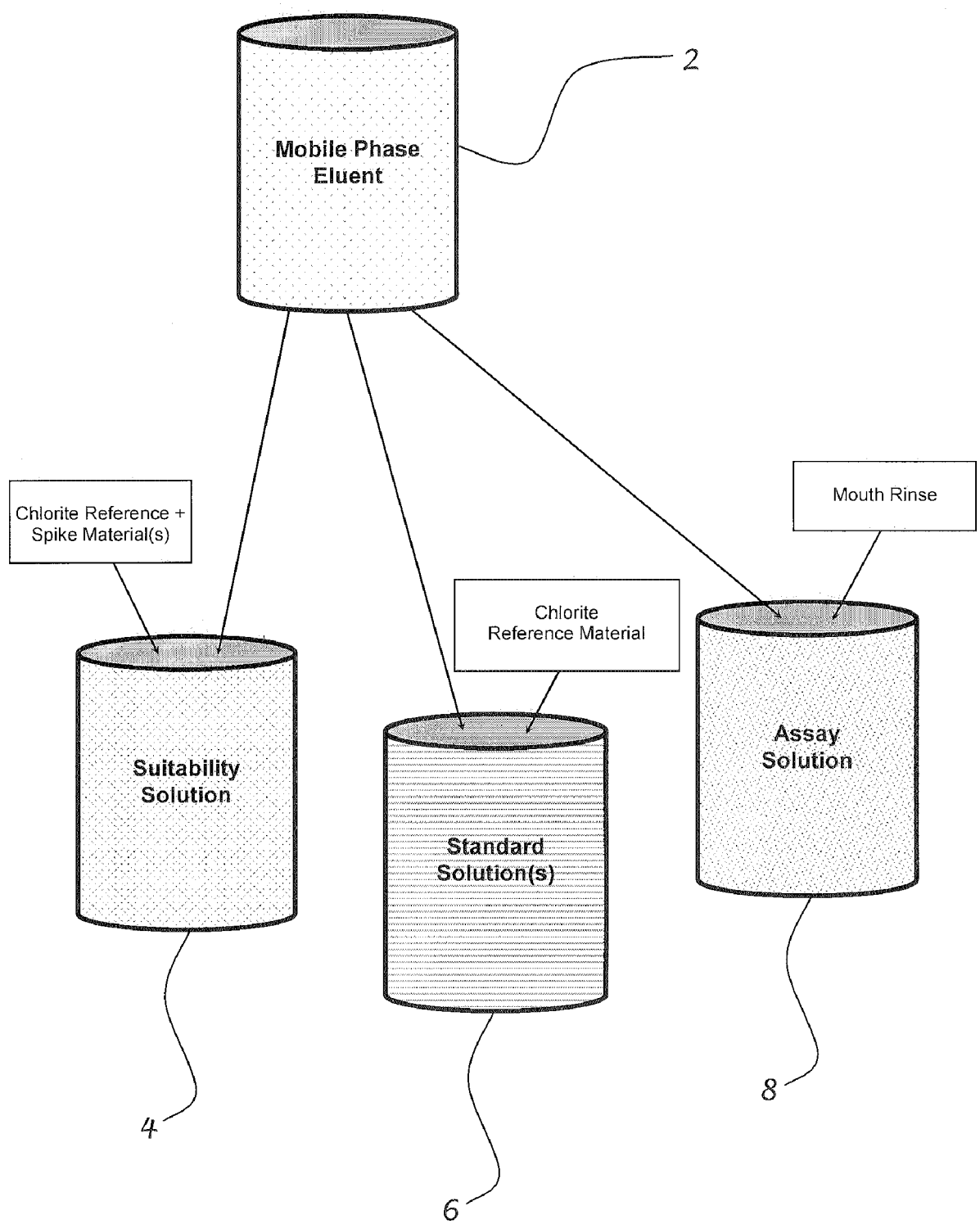
FIG. 1 illustrates that all solutions prepared for the test contain the mobile phase eluent and a specific set of additional components.

Table 1 recites the step-by-step preparation of the solutions used in the test;

Table 2 sets forth recovery results for analysis of the accuracy of the test;

Table 3 depicts results obtained when Chemist 1 ran the test;

Table 4 depicts the results obtained when Chemist 2 ran the test;

Table 5 is a comparison of the results from Chemist 1 and Chemist 2; and

Table 6 establishes the validity of the test results.

DESCRIPTION OF THE PREFERRED EMBODIMENT

Summary of the Illustrations in the Drawings and Tables

FIG. 1 shows mobile phase eluent 2, which is the base for each of the other three solutions. The components of the eluent depend on the instrumentation for the test. Based on the use of the Hitachi HPLC system, the components of the eluent are listed in detail in Table 1. The suitability solution 4 is the mobile phase eluent with the addition of a chlorite reference material and spiked with other ions of interest such as chlorate or chloride. The standard solution 6 is the mobile phase eluent with the addition of a known amount of chlorite reference material. The assay solution 8 is the mobile phase eluent with the addition of the mouth rinse (containing stabilized chlorine dioxide) being tested.

Figure 2:
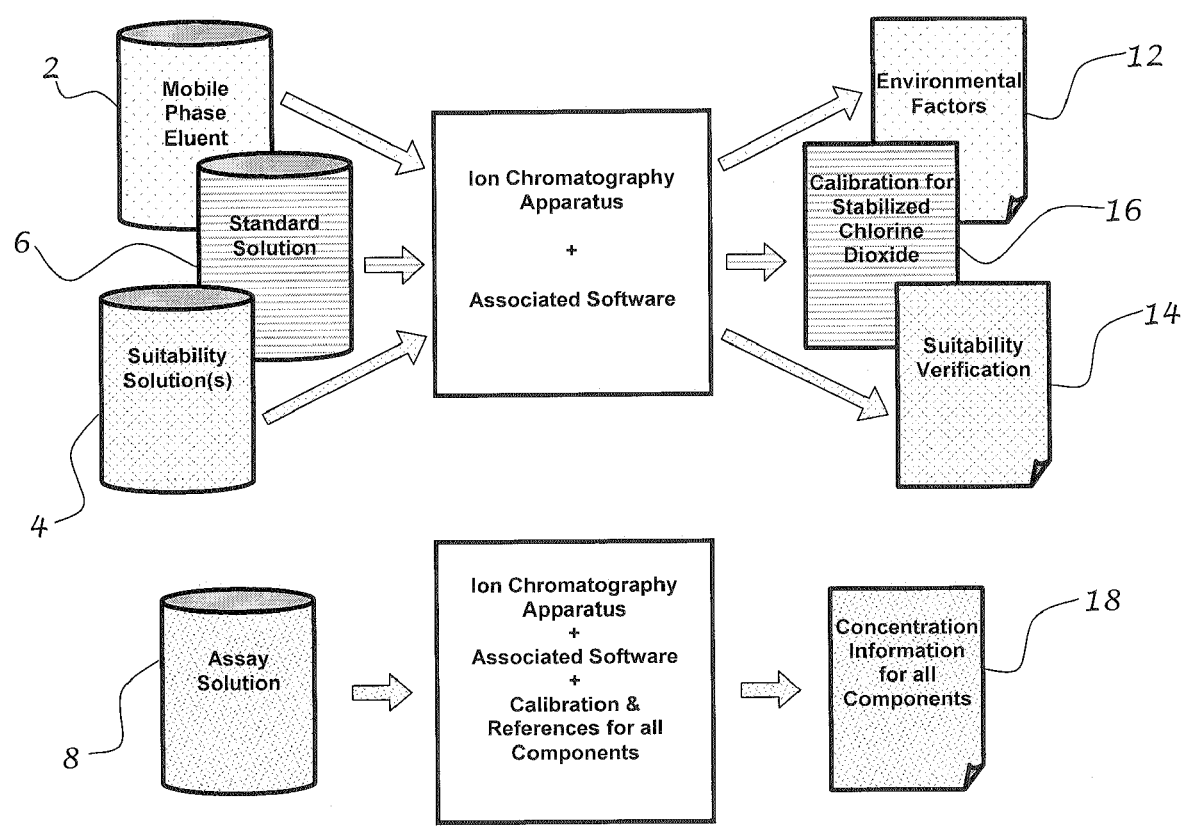
FIG. 2 illustrates the test procedure.

As shown in FIG. 2, first a baseline or indication of environmental factors 12 is determined by running the mobile phase eluent. Second, a known reference for chlorite ion is run to establish a relationship between peak size and chlorite ion concentration; this is the calibration for stabilized chlorine dioxide 16. Third, a solution containing a chlorite ion reference and another ion such as chloride is run to establish whether the peaks (commonality) for the two ions overlap; this is the suitability verification 14. Lastly, the assay solution 8 is run. Information from the prior steps is used to determine the concentration of chlorite ion 18 in the test sample without the interference of other ions.

Figure 3:
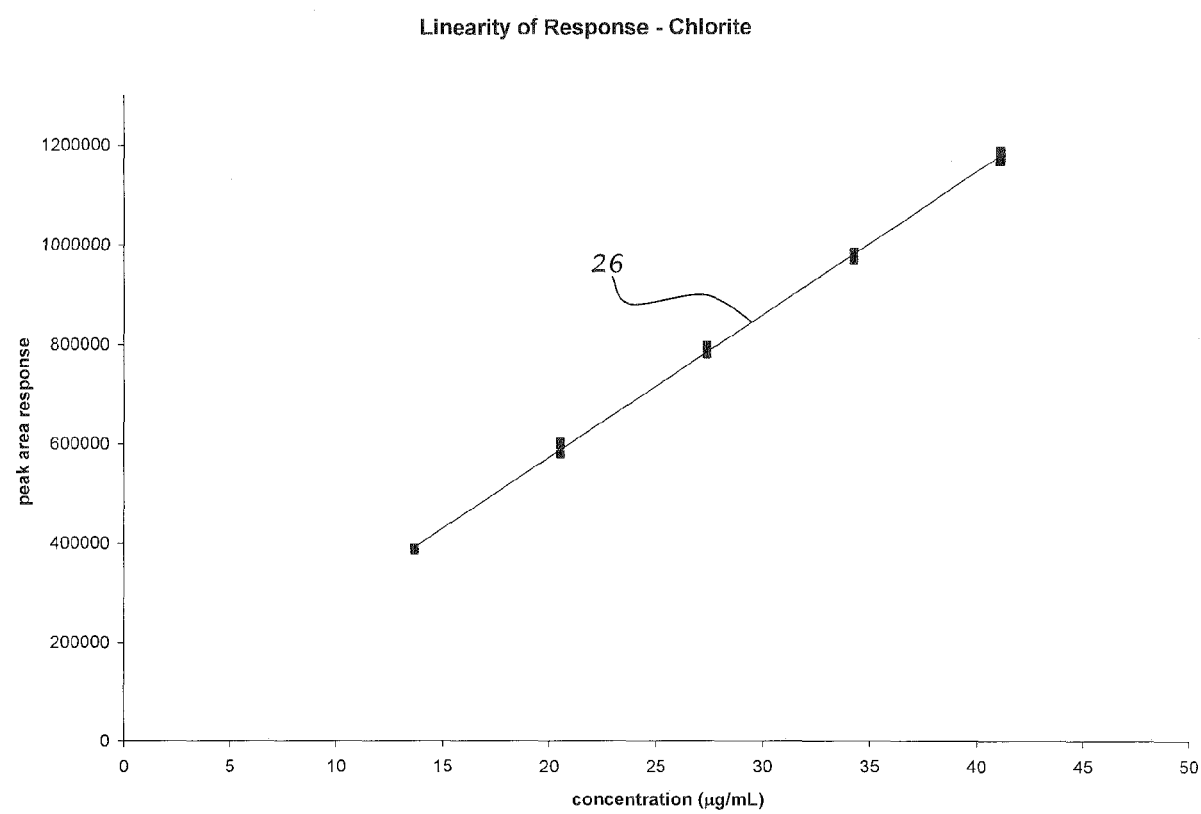
FIG. 3 illustrates the calibration of the test for chlorite ion concentration.

The calibration curve 26 for chlorite is shown in FIG. 3 as a plot of the results of 15 separate runs of varying levels of standard solution with chlorite reference material. The detector response is quantified as the area of the peak in the results of a run similar to that shown in FIG. 5, (16a). The detector response is plotted against the concentration of chlorite ion for each of the 15 runs. The calibration curve is determined by finding the line that best describes the relationship between all 15 points on the graph.

Figure 4:
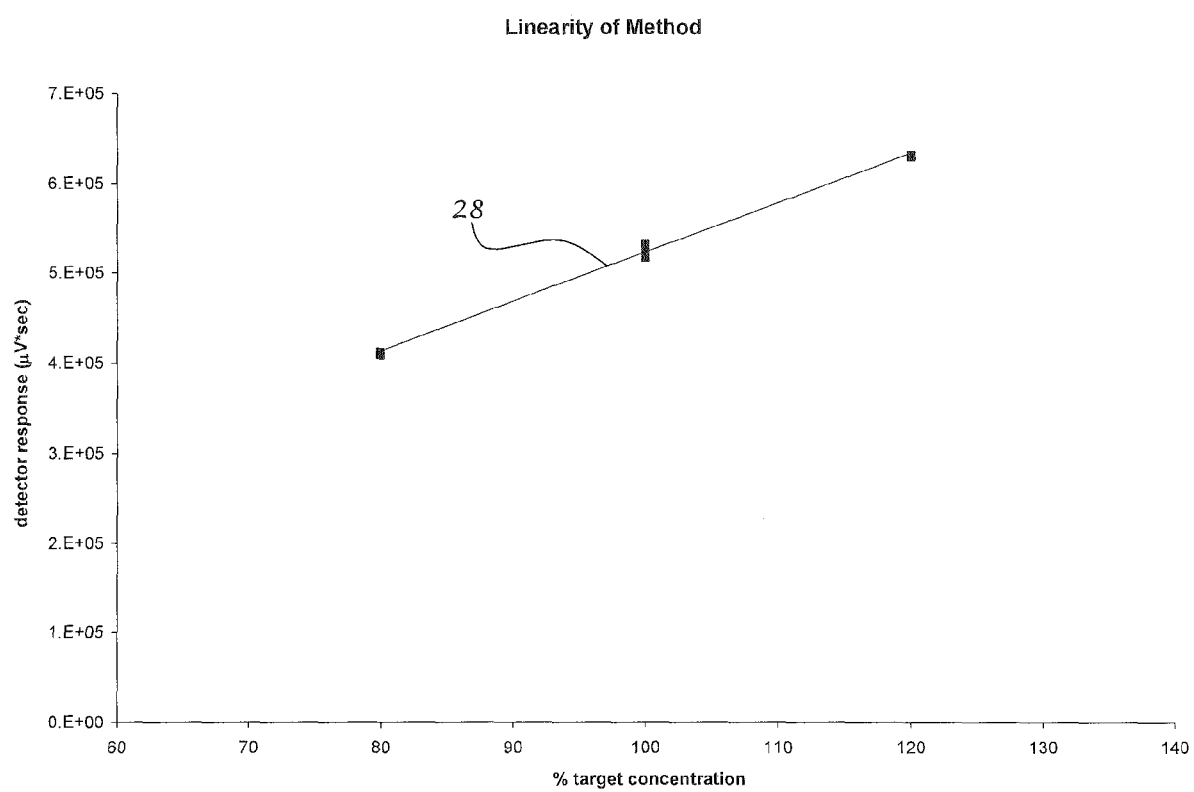
FIG. 4 illustrates that the method for preparation of the solution containing the mouth rinse does not affect the results of the test.

The linearity of the methodology shown in FIG. 4 was based on solutions that were a combination of the chlorite reference material and the stabilized chlorine dioxide-containing mouth rinse. Three concentration levels were used to test the range of the test and assure that the preparation of the solutions did not affect the test results. In this step, 10 solutions at varying levels were run. The detector response (peak area) was again plotted against concentration and the calibration for the method linearity 28 determined by finding the line that best describes the relationship between all 10 points.

Figure 5:
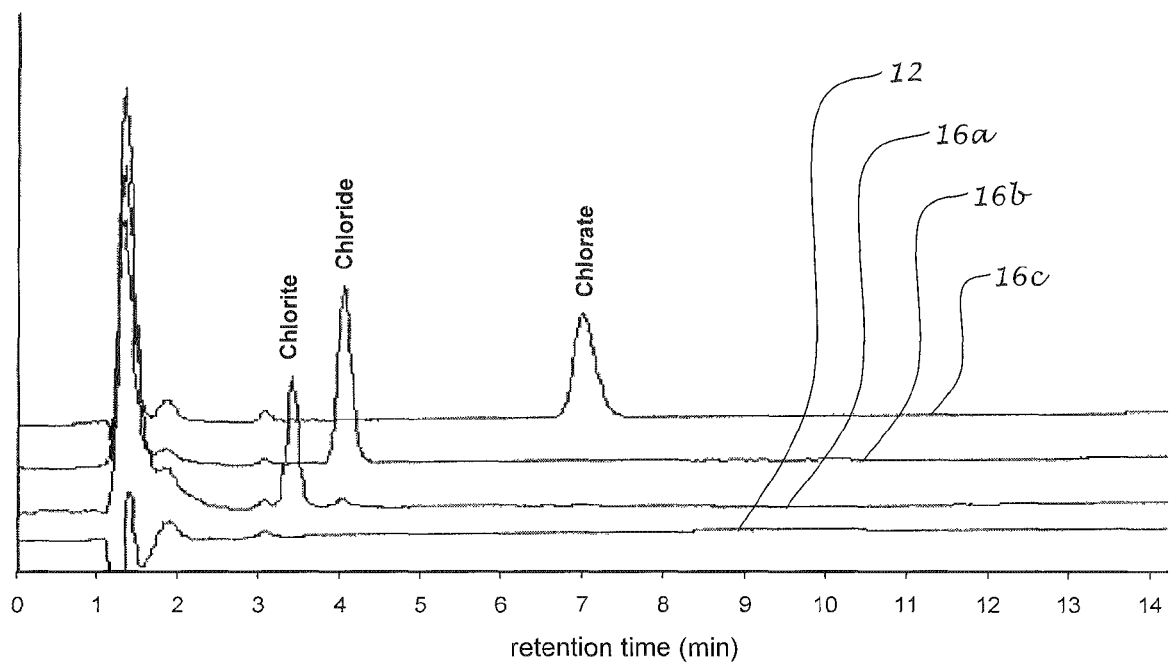
FIG. 5 illustrates a chromatogram containing the results from running four separate standard solutions.

The solutions run for the overlaid chromatogram shown in FIG. 5 were mobile phase eluent alone, standard solution containing chlorite reference material, standard solution containing chloride reference material, and standard solution containing chlorate reference material. The results of running the mobile phase eluent produce the environmental factors curve 12; running the standard solution containing a chlorite reference produced calibration information for chlorite 16a; running the standard solution containing a chloride reference produced calibration information curve 16c for chloride 16b; and running the standard solution containing a chlorate reference produced calibration information curve 16c for chlorate.

Figure 6:
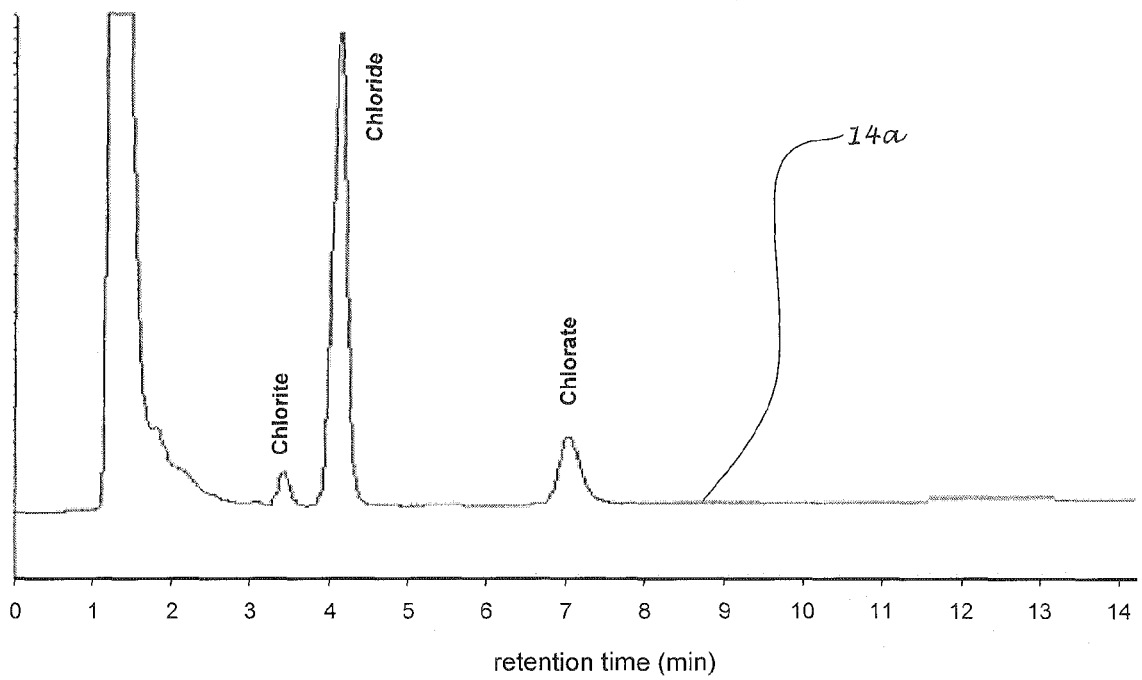
FIG. 6 illustrates a chromatogram from a suitability solution.

FIG. 6 A suitability solution of chlorite reference spiked with chloride produced the suitability verification 14a chromatogram 14a shown in FIG. 6. This indicates that the peaks for chlorite and chloride do not overlap so the concentration results for chlorite will not be clouded by possible chloride ion interference.

Table 6 is a compilation of the results from each of tests performed. Low relative standard deviation for detector response indicates low variation of detector response as a function of chlorite concentration, high resolution between peaks indicates that there is little to no interference from degradation products such as chloride or chlorate, and low relative standard deviation for retention time indicates low variation for the retention time for a material from one run to another.

Because the concentration of ions in a stabilized $ClO_2$ solution determines its safety and efficacy, measuring these concentrations is very important. The main analytical methods that are currently used for measuring $ClO_2$ content are iodometric and amperometric titration, and three calorimetric methods, one that measures the direct absorbance of solution, and two that utilize indicators, DPD glycine and Chlorophenol Red. The iodometric titration and Chlorophenol Red methods are commonly used, however, the DPD glycine and amperometirc titration are the methods currently approved by the EPA for testing water.

The drawback of using the methods listed above is the lack of sensitivity of the test method when other chlorine-containing ions are present in solution. For example, the iodometric titration relies on the oxidation power of $ClO_2$ to react in the titration. The presence of other oxidizers in the test solution will interfere with the accuracy of the titration because they will contribute to the overall oxidation and alter the reaction. Because potential degradation products of $ClO_2$ (such as $ClO^-$ and $ClO_3^-$) are also oxidizers, their concentration cannot be measured separately from $ClO_2$ using iodometric titration. The other method recommended by International Dioxide, a major supplier of chlorine dioxide, is the Chlorophenol Red method. Chlorophenol Red is a dye that is added to solution in known quantities. Oxidizers present in solution will remove the dye proportional to their concentration, and the intensity of the dye remaining is an indication of the amount of oxidizers present. Once again, the presence of $ClO_2$'s degradation products will interfere with the result of the test because they will also oxidize the dye. In addition, Chlorophenol Red is intended for measurement of $ClO_2$ dissolved in a solution, but is also used as a pH indicator. It may not accurately indicate the content of stabilized $ClO_2$ or disclose the $ClO_2$ available upon acidification, as the change in pH may affect its indication ability.

In order to get more accurate measurements of content, industries such as water treatment have adopted the use of ion chromatography for $ClO_2$ concentration determination. Ion chromatography (IC) is a particular process within the set of chromatographic analytical methods in which liquids and gases of mixed composition are analyzed by precise separation of their components. The separation is accomplished based on physical and chemical characteristics of the molecular components such as their size or charge. Following separation, the components are analyzed using electrochemical (amperometric, conductometric) or spectral (fluorescence, emission, absorbance) methods. Previous attempts to measure $ClO_2$ concentration have been clouded with the potential for interference by degradation products, but IC doesn't rely on an indicator or chemical reaction and as a result is a favorable measurement method.

Currently, no specific standards exist for the IC measurement of stabilized chlorine dioxide in a solution intended for antibacterial or other cosmetic use. However, there are a number of articles and standards that refer to chlorine dioxide, its degradation products, and methods for measurement. The American Water Works Association has published standards and articles for the measurement of $ClO_2$ in drinking water (Spectrophotometric determination of chlorine dioxide, Journal AWWA, vol. 73, 1981; Determination of Chlorine Dioxide, Chlorine, Chlorite and Chlorate in Water, Journal AWWA, vol. 76, 1984; Chlorine Dioxide by the Amperometric Method I and II, 4500-$ClO_2$ C and E; and Chlorine Dioxide by the DPD Method, 4500-$ClO_2$ D). The EPA has adopted similar standards as test methods also (Inorganic Anions by Ion Chromatography, Method 300.0 and Determination of Inorganic Anions in Drinking Water by Ion Chromatography, Method 300.1). Additionally, there are two ASTM standards that refer to chlorate, chlorite and chloride, but these are also for drinking water (Standard Test Method for Bromate, Bromide, Chlorate, and Chlorite in Drinking Water by Chemically Suppressed Ion Chromatography, ASTM standard D 6581-00; Standard Test Method for Anions in Water by Chemically Suppressed Ion Chromatography, ASTM D 4327-03, refers to chloride). Unfortunately, the literature either lists the use of methods that have limited specificity, or they are in reference to drinking water for consumption.

The lack of published standards for stabilized $ClO_2$ dosage when used as an antibacterial or as a therapeutic in oral care products provides the need for method validation to answer the questions of dosage, $ClO_2$ release, release of related undesirable chlorine species, the reliability of results and elimination of the chance for miscalculation of active ingredients. Validation of the test methods prior to their application to specific test samples can combat potential claims against the reliability of new test results. Additionally, the results obtained during certain steps in the validation process are used for the measurement itself. The FDA defines validation as follows:

> Process validation is establishing documented evidence that provides a high degree of assurance that a specific process will consistently produce a product meeting its pre-determined specifications and quality characteristics. [FDA, 1987]

In general, there are a few main components of process validation. Applicability, linearity within range in question, limits of quantitation and detection, accuracy, repeatability, reproducibility, specificity, sensitivity and robustness of the process must all be determined or quantified in order for a process to be validated.

The basic steps of the analytical procedure are to first determine a baseline, then determine how the ions/molecules potentially present are exhibited, and finally to run the sample in question and compare it to the information obtained (note FIGS. 1 and 2). The following experiments were performed in order to establish validation of current method:

Reagents and Solvents
Reference standard, for current purpose: Anthium Dioxide®
Spike Materials representing other possible components, e.g. sodium chlorate, sodium chloride
Deionized water
Eluent mobile phase, current application consisted of:
  deionized water
  Acetonitrile, HPLC grade
  1-Butanol, ACS grade
  Sodium gluconate, AR grade
  Boric acid, ACS grade
  Sodium tetraborate decahydrate, ACS grade
  Glycerine, AR grade
  Sodium hydroxide, ACS grade sample of formulation in question
Instrumentation
Hitachi HPLC system including:
  Hitachi L7200 autosampler
  Waters 431 conductivity detector
  Waters IC Pak Anion HR 4.6×75 mm (part # WAT 026765) IC column
  Hitachi L7100 gradient pumps
  Hitachi L7300 column oven
  Perkin-Elmer 970A interface
  Perkin-Elmer TotalChrom data acquisition system and processing software
  Hitachi model D-7000 Chromatography Data Station software
Setting Specifications
Isocratic HPLC pump capable of flow rate of 0.8 mL/min
HPLC Autosampler injection system capable of injection of 20 µL sample volume Prior to the validation and IC analysis of the sample in question, testing determined the interference of the environment and eluent base, whether the detector response to known components is linear and whether the retention time for known components is reproducible. Analysis of the sample in question is not possible without these preparatory steps.

First, a sample of the mobile phase eluent was passed through the column. The output of this step allowed for comparison with the sample in question, and ensured that peaks, which indicate detector response, were due to the sample and not the interaction of the eluent with the detector. Output from this step generally looks similar to that shown in FIG. 5, curve 12.

Linearity of Response

Linearity of response determined the linearity of the detector's response with respect to concentration of known components. A series of solutions were prepared, each with a known concentration of a target reference standard. Specifically, 15 solutions of sodium chlorite, target concentration being 20 µg/mL, at 5 different levels as follows: 3 at 65%, 3 at 100%, 3 at 135%, 3 at 170% and 3 at 205%, which correspond to roughly 13, 20, 27, 34, and 41 µg/mL respectively. Three replicate tests for each of five concentration levels were performed. Analysis of the response of the detector was accomplished by calculating the area under the curve of the response peak. Output from this step generally looks similar to that shown in FIG. 5, curve 16a. The retention time obtained in this step of the process is a reference for the analysis of the sample in question, i.e. if the retention time of a peak in the sample matches one from this step, they are the same substance.

Next, a graph was created that plotted detector response (of each of the 15 solutions) against the concentration, as shown in FIG. 3. The linear relationship of detector response to reference standard concentration was crucial for the analysis of the sample in question and calibrated the system. Additionally, the linear response confirmed that the size of the peak obtained in the analysis of the sample indicated the concentration of that substance. For exact concentration measurements of other substances, this step may be repeated using reference standards for chloride, chlorate and any other contaminants/degradation products. Examples of this step are provided in FIG. 5, curve 16b for chloride or curve 16c for chlorate. The linearity of response for the test set was found by calculating the coefficient of determination ($r^2$), for the calibration curve 26 ($Y=-815.311842+28568.480462 \cdot X$), as indicated in FIG. 3. The $r^2$ value was found to be 0.9990, which exceeds the minimum value for a linear response of $r^2 \geq 0.9900$. Additionally, the deviation of each individual point was not more than 10% from the calibration curve.

Linearity of Method (Assay Range)

The linearity of method step was similar to the linearity of response step, but it utilized the sample in question rather than a reference standard. In this step, a series of solutions was prepared, each having a proportion of target concentration of the sample in question. Specifically, 10 solutions at three levels as follows: 2 at 80%, 6 at 100% and 2 at 120%. The solutions were passed through the column and the detector response, again determined by the area under the curve of the peak, was plotted against the estimated concentration. The plot for response as a function of percent target concentration is illustrated in FIG. 4 and shows a linear response and the calibration curve is described by the following equation: $Y=-26621+5500.1 \cdot X$. The $r^2$ value for the response curve was 0.994, which exceeds the minimum value of $r^2 \geq 0.9900$. In addition, the maximum deviation from the curve was 1.9%, which is less than the 10% threshold for acceptance. A linear relationship of detector response to sample concentration indicated that the process of preparation does not affect the assay results.

Accuracy

The next step of the validation process, method accuracy, shows the relationship of actual measurements to the theoretical values. In this step, the sample in question was diluted to 50% and spiked with the reference standard to obtain a series of solutions with theoretical concentrations as follows: 2 at 50% (not spiked, used as a control), 2 at 80%, 2 at 90%, 2 at 100%, 2 at 110% and 2 at 120%. These solutions were passed through the column. The detector response determined the measured concentration based on the relationship established in the linearity of response step. Recovery of spiked solutions is shown in Table 2. The recovery is an indication of the accuracy of the method and shows how close the measured value is to the actual value, which, in turn, indicates the systemic error or bias that exists in the present method. In this test, the average recovery of each injection when calculated against the control averaged to a range of 99.7%-100.4%, well within the acceptance criteria of 95%-105%.

Repeatability

After determining that the process yields functional results, it is important to make sure that the process yields similar results when performed by different operators. To test this, a series of solutions with 100% target concentration was prepared by Chemist 1 using the sample in question. Chemist 1 ran two replicates of each solution and the results are shown in Table 3. Another series of solutions was prepared by Chemist 2. Chemist 2 also ran two replicates of each solution. These results of the tests are shown in Table 4. In order to meet acceptance criteria, the relative standard deviation (RSD) % of recovery values for each chemist and the combined RSD % for all values must be less than 5%. A comparison of the data from the two chemists is provided in Table 5. The RSD % for chemist 1 was 1.3%, for chemist 2 was 1.1%, and for the whole set of values was 1.7%. This comparison shows that the process is repeatable and produces similar results no matter who conducts the test based on recovery and standard deviation.

Specificity

The specificity analysis in the validation was extremely important because it determined the ability of IC to separate the chlorite in solution from the other ions potentially present, namely chloride, chlorate and hypochlorite. Additionally, the specificity analysis was done to demonstrate the lack of interference from a blank presentation, matrix sample ingredients and possible impurities in the elution zone of the peak of interest. Representation of the data is graphical, either as overlaid chromatograms or as spiked solution chromatograms. These chromatograms show the separation between peaks. FIG. 5 is an overlaid chromatogram of the mobile phase eluent (curve 12), the standard solution (curve 16a), a chloride ion solution (curve 16b), and a chlorate ion solution (curve 16c). Curve 14a in FIG. 6 is an example of the chromatogram of a suitability solution spiked with chloride.

The analysis showed that no interference from the blank, matrix, impurities or degradation products existed, which met the acceptance criteria. If the peaks were not separate, the area under the curves could be a net result of two components, which would make analysis of the solution in question very difficult. (This is what happens with indicator and chemical reaction methods.) If estimates are adequate for concentration measurements of contaminants and degradation products, this step is used to indicate the approximate retention time and/or concentration of those components based on detector response.

System Suitability

An analysis on system suitability was done using a comparison of the data from the previous validation tests. The results from each of the sections of the validation procedure are compared in Table 6. The evaluation showed that the RSD % for peak retention time was a maximum of 0.2%, well within the limit for acceptance criteria of peak retention time RSD %≧5.0%. It also shows that the maximum RSD % for peak response was 2.79%, which was less than the acceptance criteria of peak response RSD %≧3.0%. Additionally, the resolution between the peaks for chlorite and chlorate peaks was 9.0, which is well above the threshold of resolution of not less than 1.8.

Safety

Previous patents have addressed safety concerns surrounding the use of chlorine-ion-containing ingredients for use in consumer products, especially those products intended for oral care [U.S. Pat. Nos. 4,689,215; 6,132,702; 6,231,830]. Although the intended oral care product would be used in the oral cavity and expectorated, studies have shown that a certain percentage of the product is typically ingested during its use. The percent of ingestion is highly dependent on the age of the person using the product. That is, children are much more likely to ingest during use than adults (age 2-4=34.9%, age 5-7=13.9%, age 11-13=6.4%, age 20-35=2.9% [Barnhart, 1973]). In addition to the possibility for unintended ingestion, prior concentration testing that did not use highly selective analytical methods and has the potential to allow the inclusion of more dangerous components in the composition. Not only does this intensify the need for extensive safety testing, but it also implies a decrease in potential efficacy as the actual concentration of the composition is lower than intended.

A dose of 15 mL, two times per day, of 0.1% stabilized chlorine dioxide would correspond to 30 mg total exposure. Using an adult human weight range of 110-180 lbs., which is roughly equivalent to 50-80 kg, the daily dose per kilogram would be 0.6-0.375 mg/kg/day. Overestimating the percent ingestion for an adult to 10%, the exposure due to ingestion would be 0.06-0.0375 mg/kg/day. In a study using Sprague-Dawley rats, Daniel, et al. reported that there were no toxicologically significant effects on haematology, blood biochemistry, or organ weights due to exposures on the order of 0, 2, 4, 6, and 12 mg/kg/day (male) and 0, 2, 5, 8, and 15 mg/kg/day (female), of aqueous chlorine dioxide in drinking-water for 90 days. The only target tissue that was identified was the nasal cavity, which showed an increased incidence of goblet cell hyperplasia, squamous metaplasia, and inflammatory responses. Additionally, no deaths were reported, even at exposures as high as 11.5 mg/kg/day (male) and 14.9 mg/kg/day (female) [Daniel, 1990. In another study done to assess the safety of $ClO_2$-treated drinking water, Michael, et al. exposed 197 humans for three months to treated water containing mean chlorite concentration of 10.3 mg/day, with a range of 0-39.4 mg/day. Using hematologic serum chemistry measurements, the study failed to show any significant adverse effects [Michael, 1981]. Based on the low dose per kilogram per day during normal use of the oral care product described, and considering the new data differentiating the components of the composition, the safety of the product is well established.

We claim:

1. A method for determining the effective concentration of stabilized chlorine dioxide in a solution; said method comprising the steps of:
   a. creating a mobile phase eluent as a function of the ion chromatography apparatus to be used;
   b. further creating a suitability solution by adding a chlorite reference material to the mobile phase eluent;
   c. spiking the suitability solution with ions of interest selected from the group consisting of chlorate and chloride;
   d. yet further creating a standard solution by adding a known amount of chlorite reference material to the mobile phase eluent;
   e. still further creating an assay solution by adding a solution of stabilized chlorine dioxide being tested to the mobile phase eluent;
   f. obtaining an indication of environmental factors by analyzing the mobile phase eluent with the ion chromatography apparatus;
   g. further obtaining an indication of the peak size and chlorite ion concentration by analyzing the standard solution with the ion chromatography apparatus;
   h. yet further obtaining an indication of the commonality between the two chlorate and chlorite ions by analyzing the spiked suitability solution with the ion chromatography apparatus;
   i. still further obtaining an indication of the chlorite ion in the assay solution by analyzing the assay solution with the ion chromatography apparatus; and
   j. comparing the indications obtained in steps f, g and h with the indication obtained in step i) to determine the concentration of chlorite ions in the assay solution.

2. The method as set forth in claim 1, including the step of providing a graph of the indications obtained.

3. The method as set forth in claim 1, including the step of quantifying the response of the ion chromatography apparatus to the concentration of the chlorite ion.

4. The method as set forth in claim 1 wherein step e) is carried out for each of several solutions of stabilized chlorine dioxide having different levels of concentration to obtain a corresponding number of assay solutions and the steps of carrying out step i) for each assay solution and plotting the indications obtained to determine linearity of the indications.

5. The method as set forth in claim 1, including the step of generating calibration information for chlorite.

6. The method as set forth in claim 1, including the step of generating calibration information for chloride.

7. The method as set forth in claim 1, including the step of generating calibration information for chlorate.

8. The method as set forth in claim 1, including the step of creating a chromatogram for each indication obtained by exercise of steps f, g, h and i.

9. The method as set forth in claim 1, including the step of creating a chromatogram for selected ones of the indications obtained by exercise of steps f, g, h and i.

10. The method as set forth in claim 1, including the step of correlating the amount of chlorite present as a function of the concentration of the stabilized chlorine dioxide in the assay solution.

11. The method as set forth in claim 1, including the step of correlating the amount of chlorate present as a function of the concentration of the stabilized chlorine dioxide solution in the assay solution.

12. The method as set forth in claim 1, including the step of correlating the amount of chloride present as a function of the concentration of the stabilized chlorine dioxide solution in the assay solution.

13. A method for determining the degree of chlorite present in a known concentration of stabilized chlorine dioxide in a solution, said method comprising:
   a. creating a mobile phase eluent as a function of the ion chromatography apparatus to be used;
   b. further creating a suitability solution by adding a chlorite reference material to the mobile phase eluent;
   c. spiking the suitability solution with ions of interest selected from the group consisting of chlorate and chloride;
   d. yet further creating a standard solution by adding a known amount of chlorite reference material to the mobile phase eluent;
   e. still further creating an assay solution by adding a solution of stabilized chlorine dioxide of known concentration to the mobile phase eluent;
   f. obtaining an indication of environmental factors by analyzing the mobile phase eluent with the ion chromatography apparatus;
   g. further obtaining an indication of the peak size and chlorite ion concentration by analyzing the standard solution with the ion chromatography apparatus;
   h. still further obtaining an indication of the chlorite ion in the assay solution by analyzing the assay solution with the ion chromatography apparatus; and
   i. correlating the amount of chlorite present as a function of the concentration of the stabilized chlorine dioxide.

14. The method as set forth in claim 13, including the step of determining the concentration of chlorite present as a function of the concentration of the stabilized chlorine dioxide.

15. A method for determining the effective concentration of stabilized chlorine dioxide in a solution, said method comprising the steps of:
   a. creating a mobile phase eluent as a function of the ion chromatography apparatus to be used;
   b. creating a suitability solution by adding a chlorite reference material to the mobile phase eluent;
   c. yet further creating a standard solution by adding a known amount of chlorite reference material to the mobile phase eluent;
   d. still further creating an assay solution by adding a solution of stabilized chlorine dioxide being tested to the mobile phase eluent;
   e. further obtaining an indication of the peak size and chlorite ion concentration by analyzing the standard solution with the ion chromatography apparatus;
   f. further obtaining an indication of the chlorite ion in the assay solution by analyzing the assay solution with the ion chromatography apparatus; and
   g. correlating the amount of chlorite present as a function of the concentration of the stabilized chlorine dioxide.

16. The method as set forth in claim 15, including the step of determining the concentration of chlorite as a function of the concentration of the stabilized chlorine dioxide.

* * * * *